United States Patent
Brunneke et al.

(10) Patent No.: US 7,367,742 B2
(45) Date of Patent: May 6, 2008

(54) BALL AND SOCKET JOINT

(75) Inventors: Hans-Gerd Brunneke, Osnabrück (DE); Ralf Kunze, Bad Essen (DE)

(73) Assignee: ZF Lemförder Metallwaren AG, Stemwede-Dielingen (DE)

( * ) Notice: Subject to any disclaimer, the term of this patent is extended or adjusted under 35 U.S.C. 154(b) by 492 days.

(21) Appl. No.: 10/381,615

(22) PCT Filed: Aug. 20, 2002

(86) PCT No.: PCT/DE02/03101

§ 371 (c)(1),
(2), (4) Date: Mar. 26, 2003

(87) PCT Pub. No.: WO03/019022

PCT Pub. Date: Mar. 6, 2003

(65) Prior Publication Data

US 2004/0037619 A1     Feb. 26, 2004

(30) Foreign Application Priority Data

Aug. 24, 2001    (DE) .................. 101 40 683

(51) Int. Cl.
*F16C 11/06*     (2006.01)
(52) U.S. Cl. ................ 403/122; 403/27; 403/135
(58) Field of Classification Search .......... 403/27, 403/122, 135; 384/277, 448; 340/454, 686.1, 340/686.2
See application file for complete search history.

(56) References Cited

U.S. PATENT DOCUMENTS

| | | | | |
|---|---|---|---|---|
| 1,361,000 A | * | 12/1920 | Blain et al. | 384/191 |
| 3,102,759 A | * | 9/1963 | Stewart | 384/276 |
| 3,602,560 A | * | 8/1971 | Memmel | 403/140 |
| 4,092,053 A | * | 5/1978 | Riegler et al. | 384/448 |
| 4,549,830 A | * | 10/1985 | Mette | 403/134 |
| 4,679,957 A | * | 7/1987 | Bauer | 403/27 |

(Continued)

FOREIGN PATENT DOCUMENTS

DE         3416343 A  * 11/1985

(Continued)

OTHER PUBLICATIONS

English Translation of Japanese patent, JP-56-006911A, PTO-2006-1712.*

*Primary Examiner*—James M. Hewitt
*Assistant Examiner*—Ernesto Garcia
(74) *Attorney, Agent, or Firm*—McGlew and Tuttle, P.C

(57) ABSTRACT

A ball-and-socket joint for a motor vehicle, especially for the chassis of the motor vehicle has a ball-and-socket joint housing (i), which has a joint opening and in which a bearing shell (5) made of an insulating material is arranged. A ball pivot (4) is made of an electrically conductive material and has a joint ball (2) and a pivot (3) mounted rotatably and pivotably with its joint ball (2) in the bearing shell (5) and protrudes with its pivot (3) from the ball-and-socket joint housing (1) through the joint opening. An electrode (14) is arranged in the wall (12) of the bearing shell (5) at a spaced location from the joint ball (2), and the electrode (14) and the joint ball (2) are electrically insulated against each other via the bearing shell (5).

17 Claims, 2 Drawing Sheets

U.S. PATENT DOCUMENTS

| | | | |
|---|---|---|---|
| 4,749,299 A * | 6/1988 | Swanson | 403/27 |
| 5,011,321 A * | 4/1991 | Kidokoro | 403/140 |
| 5,701,119 A * | 12/1997 | Jurras, III | 384/448 |
| 6,152,637 A | 11/2000 | Maughan | |
| 6,366,201 B1 * | 4/2002 | Hanisko | 340/454 |
| 6,384,721 B1 * | 5/2002 | Paielli | 340/454 |
| 6,533,491 B1 * | 3/2003 | Redele | 403/27 |
| 6,632,252 B1 * | 10/2003 | Kyrtsos | 340/449 |
| 6,644,883 B2 * | 11/2003 | Davis | 403/134 |
| 6,773,197 B2 * | 8/2004 | Urbach | 403/135 |
| 7,048,461 B2 * | 5/2006 | Williams | 403/27 |
| 7,063,480 B2 * | 6/2006 | Ersoy et al. | 403/135 |
| 2002/0149565 A1 * | 10/2002 | Sako | |

FOREIGN PATENT DOCUMENTS

| | | |
|---|---|---|
| DE | 195 46 084 | 5/1997 |
| DE | 199 18 869 | 10/1999 |
| DE | 100 09 054 | 9/2001 |
| EP | 0 632 207 A1 | 1/1995 |
| EP | 1 042 155 | 10/2000 |
| EP | 1400712 A2 * | 3/2004 |
| FR | 2833321 A1 * | 6/2003 |
| JP | 56006911 | 1/1981 |
| JP | 56006911 A * | 1/1981 |
| JP | 62017421 A * | 1/1987 |
| JP | 62132020 A * | 6/1987 |
| JP | 62132021 A * | 6/1987 |
| JP | 62137407 A * | 6/1987 |
| JP | 63292001 A | 11/1988 |
| JP | 63293318 A * | 11/1988 |
| SU | 815332 | 3/1981 |
| WO | WO 99/35020 | 7/1999 |

* cited by examiner

BALL AND SOCKET JOINT

FIELD OF THE INVENTION

The present invention pertains to a ball-and-socket joint for a motor vehicle, especially for the chassis of the motor vehicle, with a ball-and-socket joint housing which has a joint opening and in which a bearing shell manufactured from an insulating material is arranged, with a ball pivot, which is made of an electrically conductive material, has a joint ball and a pivot, is mounted with its joint ball rotatably and pivotably in the bearing shell and protrudes with its pivot from the ball-and-socket joint housing through the joint opening.

BACKGROUND OF THE INVENTION

Such a ball-and-socket joint is described in the German patent application DE 100 09 054.0, where the ball-and-socket joint housing made of an electrically conductive material is connected via electric lines to an evaluating unit, by means of which excessive wear of the bearing shell, which is characterized by the direct contact of the joint ball with the ball-and-socket joint housing, can be detected.

DE 199 18 869 A1 discloses a ball-and-socket joint for vehicle steering knuckles, which has a joint housing and a joint pin, which is mounted rotatably and deflectably in a two-part bearing shell made preferably from a polymeric material by means of a spherical bearing surface, wherein the bearing shell itself is arranged in the joint housing. A wear indicator insert, which protrudes from the sealing washer in the nonworn state of the ball-and-socket joint on the side of the sealing washer facing away from the bearing shell, is inserted into a sealing washer fixed in the housing under pretension against the bearing shell. This pretension decreases with increasing wear of the ball-and-socket joint, so that the wear indicator insert can be moved by an operator and can be pressed into the sealing washer from the side of the sealing washer facing away from the bearing shell. When the wear indicator insert can be moved or pressed into the sealing washer to the extent that it no longer protrudes from the sealing washer on the side of the sealing washer facing away from the bearing shell, this indicates that the ball-and-socket joint is worn.

SUMMARY OF THE INVENTION

The object of the present invention is to provide a ball-and-socket joint in which excessive wear of the bearing shell can be detected in a simple manner without an operator having to perform a manual checking at the site of the ball-and-socket joint.

A ball-and-socket joint is provided according to the present invention for a motor vehicle, especially for the chassis of the motor vehicle, where the ball-and-socket joint has a ball-and-socket joint housing which has a joint opening and in which a bearing shell made of an insulating material is arranged and has a ball pivot which is made of an electrically conductive material and has a joint ball and a pivot. The ball pivot is mounted with its joint ball rotatably and pivotably in the bearing shell and protruding with its pivot from the ball-and-socket joint housing through the joint opening. An electrode is arranged in the wall of the bearing shell at a spaced location from the joint ball, the electrode and the joint ball being electrically insulated against each other via the nonworn bearing shell.

Electrically insulating material of the bearing shell, which electrically insulates the joint ball against the electrode, is located between the electrode and the joint ball in the nonworn state of the bearing shell. The thickness of the material of the bearing shell present between the electrode and the joint ball, which thickness is set at the time of the manufacture, decreases with increasing wear until the joint ball directly touches the electrode. This state of contact can be measured by means of an electric evaluating device, which is connected to both the electrode and the ball pivot via electric lines.

Using an evaluating means, a signal can be sent to the vehicle driver by activating an optical or acoustic signal transmitter in the interior space of the vehicle when the joint ball and the electrode touch each other. However, it is possible when there is an electric contact between the electrode and the joint ball to send a signal to a digital computer provided in the motor vehicle or to another means storing readable information, so that an information characterizing the wear of the ball-and-socket joint is stored in the memory, which can be polled, e.g., in the case of maintenance work or, e.g., also via a radio signal at a receiver located at another location (e.g., in a workshop or at the motor vehicle manufacturer).

How much material can be removed from the bearing shell until the contact between the joint ball and the electrode is closed and the bearing shell must be considered worn can be determined from the thickness of the material of the bearing shell that is present between the electrode and the joint ball at the time of the manufacture of the joint ball.

The electric evaluating device, which can be or is connected to the ball-and-socket joint according to the present invention via electric lines, may be arranged at a distance from the site of the ball-and-socket joint, so that an excessive wear of the bearing shell can be detected in a simple manner without an operator having to perform a manual checking at the site of the ball-and-socket joint.

The electrode may be designed as a pin arranged in the bearing shell. This pin may be designed as a cylindrical pin or as a pin that can be screwed in with a thread.

However, the electrode is preferably designed as a ring-shaped electrode (ring electrode), so that the wear can be monitored independently from the direction of the principal load of the ball-and-socket joint. Thus, the ball-and-socket joint does not have to be aligned with the electrode to the direction of the principal load during the installation in the vehicle. It is correspondingly also possible in the sense of the present invention to provide a plurality of electrodes arranged in a distributed pattern within the bearing shell.

Furthermore, it is possible to design the electrode as a foil or printed circuit board enclosed in the material of the bearing shell or as a vapor-deposited or metallized layer.

If the ball-and-socket joint housing is made of an electrically conductive material and the electrode is connected to the ball-and-socket joint housing, an electric contact may also develop between the ball pivot and the electrode in the nonworn state of the bearing shell when the ball pivot is deflected in relation to the ball-and-socket joint housing to the extent that the transition area of the ball pivot, which is present between the joint ball and the pivot, abuts the edge of the ball-and-socket joint housing surrounding the joint opening. The electric contact between the joint ball and the electrode would be closed in this case only via the ball-and-socket joint housing rather than directly, and special insulation measures are therefore necessary to avoid this. It is therefore proposed that the ball pivot be provided with a collar made of an electrically insulating material in the transition area provided between the joint ball and the pivot. An electric contact is thus reliably prevented from developing between the ball pivot and the edge of the ball-and-socket joint housing surrounding the joint opening.

The components used in the chassis of a motor vehicle are usually made of a metallic material and consequently an electrically conductive material. This may lead to the undesired effect that the electrode and the ball pivot of the ball-and-socket joint mounted in the chassis are indirectly connected to one another electrically via the chassis parts if the ball-and-socket joint housing is made of an electrically conductive material and the electrode is not insulated electrically against the ball-and-socket joint housing. According to a variant of the ball-and-socket joint according to the present invention, the pivot is therefore surrounded by an electrically insulating material in a ring-shaped pattern on its end area facing away from the joint ball. Thus, an electrically insulating layer is present between the ball pivot and the chassis part to which the pivot is fastened, as a result of which a direct electric connection is reliably prevented from developing between the ball pivot and the chassis part in question.

If the ball pivot surrounded by electrically insulating material in a ring-shaped pattern is connected to a chassis part via an additional fastening means, this fastening means shall preferably also be arranged or designed in an electrically insulated manner in relation to the ball pivot and/or the chassis part. If, e.g., the pivot is provided with a thread at its end facing away from the joint ball and the fastening means is designed as a nut that is made of a metallic material and can be screwed onto the thread, an insulating plain washer may be arranged between the nut and the chassis part in order to prevent an electrically conductive contact between the nut and the chassis part.

The electrode may be designed, furthermore, as a projection that is made in one piece with the ball-and-socket joint housing and is aligned with the joint ball in the interior of the ball-and-socket joint housing. However, the electrode is preferably designed as a separate component, so that the bearing shell and the electrode can be assembled before the mounting of the bearing shell into one assembly unit, which is then inserted into the ball-and-socket joint housing.

The electrode may be sealed in the plastic housing. However, the electrode is preferably inserted into a recess that is provided in the wall of the bearing shell and is open toward the ball-and-socket joint housing, the electrode being fixed in the recess, e.g., by means of a snap connection or with the use of an adhesive.

The recess may be designed in the form of a hole for receiving a pin-shaped electrode or in the form of an internal thread for receiving an electrode designed as a threaded pin. However, the recess is preferably an annular groove, so that the electrode can be inserted into the annular groove at any point of the annular groove. However, the electrode designed as a ring electrode is especially preferably inserted into the annular groove.

The electrode may be in electric contact with the ball-and-socket joint housing, the electrode being able to be contacted via a contact of the ball-and-socket joint housing. However, the electrode is preferably electrically insulated against the ball-and-socket joint housing, so that electrical insulation of the ball pivot against the ball-and-socket joint housing and/or against a chassis part connected to the ball-and-socket joint can be eliminated. Furthermore a lubricant introduced into the interior space of the ball-and-socket joint cannot adversely affect the wear measurement any longer if the ball-and-socket joint housing is made of an electrically conductive material, because leak currents between the electrode and the joint ball via the ball-and-socket joint housing and the lubricant, which leak currents distort the wear measurement, are now reliably prevented from developing before the onset of the state of complete wear. The state of complete wear is characterized here by the direct electric contact between the electrode and the joint ball.

An electric line necessary for contacting the electrode may be led out of the ball-and-socket joint housing via the joint opening. To prevent undesired foreign substances from penetrating through this joint opening, corresponding sealing measures should, of course, be taken against the environment.

It is also conceivable to arrange, e.g., a contact device designed as a plug-type connection on the ball-and-socket joint housing. However, a duct, through which an electric line, which is connected to the electrode and is electrically insulated against the ball-and-socket joint housing, extends out of the ball-and-socket joint housing, is preferably provided in the housing. Thus, the electric line does not have to be led through a sealing bellows, or be brought into contact with one of the sealing surfaces of a sealing bellows, as a result of which possible losses of tightness can be prevented in the area of the joint opening.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
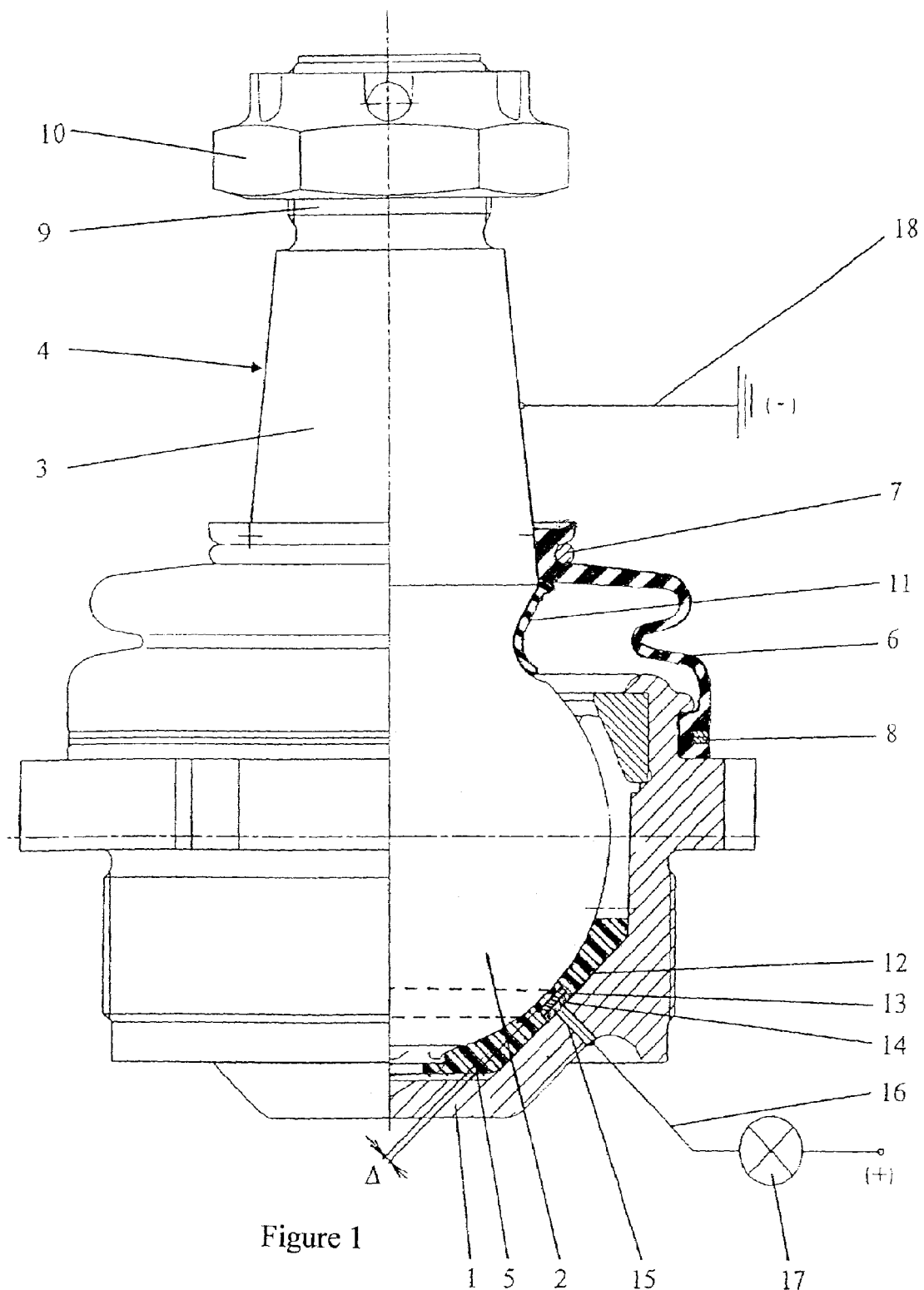
FIG. 1 is a partially cut-away view of an embodiment of the ball-and-socket joint according to the present invention.

Referring to the drawings in particular, The figure shows a partially cut-away view of an embodiment of the ball-and-socket joint according to the present invention. A ball pivot 4 having a joint ball 2 and a pivot 3 is mounted rotatably and pivotably in a bearing shell 5 in a ball-and-socket joint housing 1. A sealing bellows 6, which is sealingly in contact with the ball-and-socket joint housing 1 by one of its ends and with the pivot 3 by its other end and prevents dirt and water from penetrating into the interior of the ball-and-socket joint housing 1, is arranged between the ball-and-socket joint housing 1 and the ball pivot 4. The two ends of the sealing bellows 6 are centripetally pretensioned via a straining ring 7 and 8 each. A thread 9, on which a nut 10 is screwed, is provided at the end area of the pivot 3 facing away from the joint ball 2. Furthermore, the ball pivot 4 is surrounded by a collar 11 made of an electrically insulating material in the transition area between the joint ball 2 and the pivot 3.

A recess 13, which is open toward the ball-and-socket joint housing 1 and into which an electrode 14 is inserted and fixed by means of an adhesive, is provided in the wall 12 of the bearing shell 5. Via a first electric line 16 led through a duct 15 provided in the ball-and-socket joint housing 1, the electrode 14 is electrically connected to an incandescent lamp 17 (or another optical signal transmitter), whose other terminal is connected to the positive pole (+) of a power source. Both the first electric line 16 and the electrode 14 are designed here such that they are electrically insulated against the ball-and-socket joint housing 1.

The ball pivot 4 is connected with its pivot 3 to the negative pole (−) of the power source via a second electric line 18, so that a closed electric circuit is formed in case of an electrical connection between the ball pivot 4 and the electrode 14, and the incandescent lamp 17 goes on.

The maximum allowable wear of the bearing shell 5 can be set by selecting the thickness Δ of the area of the bearing shell 5 located between the electrode 14 and the joint ball 2 at the time of the manufacture of the ball-and-socket joint, because the distance Δ decreases with increasing wear until an electric contact is finally formed between the joint ball 2 and the electrode 14. The circuit is closed at this moment, so that the incandescent lamp 17 goes on. If the incandescent lamp 17 is arranged in the interior space of the motor vehicle, the driver of the vehicle can determine from the lighting of the incandescent lamp 17 that the bearing shell 5 of the ball-and-socket joint is worn.

Figure 2:
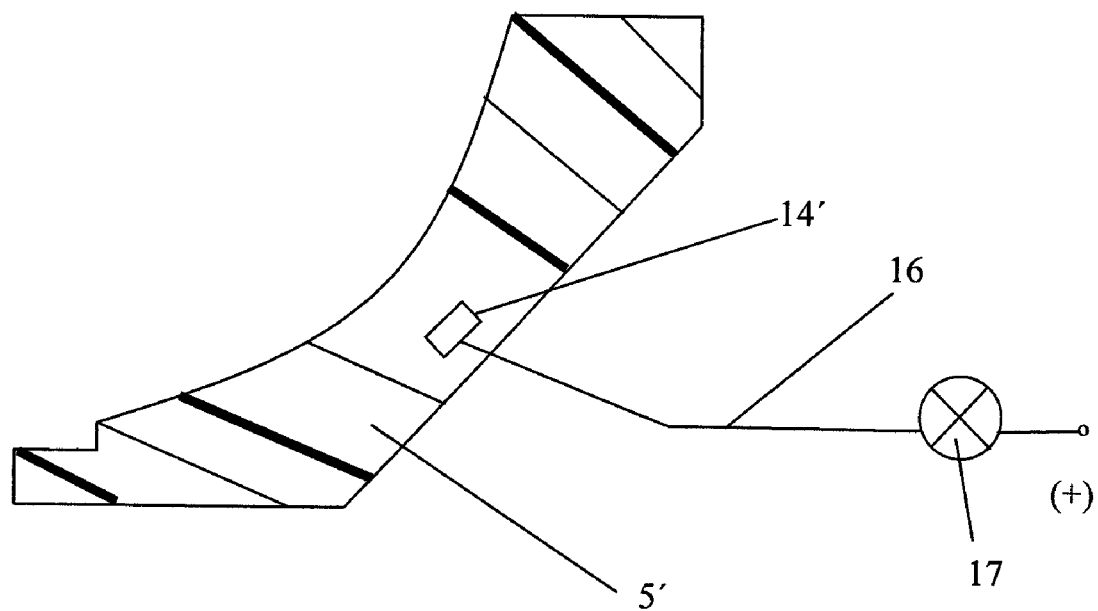
FIG. 2 is a sectional view of the electrode in the form of a printed circuit board enclosed within a bearing shell and connected to an incandescent lamp.

FIG. 2 is a sectional view of the electrode in the form of a printed circuit board 14'. The printed circuit board 14' is located in the bearing shell 5'. The electric line 16 connects the printed circuit board 14' to the incandescent lamp 17.

While specific embodiments of the invention have been shown and described in detail to illustrate the application of the principles of the invention, it will be understood that the invention may be embodied otherwise without departing from such principles.

The invention claimed is:

1. A ball-and-socket joint for a motor vehicle, the ball-and-socket joint comprising:
    a ball-and-socket joint housing with a joint opening, said ball-and-socket joint housing being composed of an electrically conductive material;
    a bearing shell made of an insulating material arranged in said housing;
    a ball pivot made of an electrically conductive material, the ball pivot having a joint ball and a pivot mounted rotatably and pivotably with said joint ball in said bearing shell and protruding with said pivot from said ball-and-socket joint housing through said joint opening;
    an electrode arranged in a wall of said bearing shell at a spaced location from said joint ball, said electrode and said joint ball being electrically insulated with respect to each other via said bearing shell disposed between said electrode and said joint ball, said electrode being electrically insulated with respect to said ball-and-socket joint housing; and
    an electrode signal connection line connected to said electrode and extending from said electrode through said ball-and-socket joint housing, said electrode signal connection line being electrically insulated with respect to said ball-and-socket joint housing.

2. A ball-and-socket joint in accordance with claim 1, wherein said electrode has a ring-shaped design.

3. A ball-and-socket joint in accordance with claim 1, wherein said ball pivot is surrounded by a collar made of an electrically insulating material in a transition area between said joint ball and said pivot.

4. A ball-and-socket joint in accordance with claim 1, wherein said pivot is surrounded by electrically insulating material in a ring-shaped pattern at least at its end area facing away from said joint ball.

5. A ball-and-socket joint in accordance with claim 1, wherein said electrode is designed as a separate component.

6. A ball-and-socket joint in accordance with claim 1, wherein a recess, which is open toward said ball-and-socket joint housing and into which said electrode is inserted, is provided in said wall of said bearing shell.

7. A ball-and-socket joint in accordance with claim 6, wherein said recess is designed as an annular groove.

8. A ball-and-socket joint in accordance with claim 1, wherein said electrode signal connection line is an electrically insulated line, said ball-and-socket joint housing having a duct, through which said electrically insulated electric line, which is connected to said electrode and is electrically insulated with respect to said ball-and-socket joint housing, extends from said ball-and-socket joint housing, said electrically insulated line being provided in and extending through said ball-and-socket joint housing, said joint ball having a diameter that is greater than a transverse diameter of said duct.

9. A ball-and-socket joint for a motor vehicle, the ball-and-socket joint comprising:
    an electrically conductive ball-and-socket joint housing with a joint opening;
    a bearing shell made of an insulating material arranged in said housing;
    a ball pivot made of an electrically conductive material, the ball pivot having a joint ball and a pivot mounted rotatably and pivotably with said joint ball in said bearing shell and protruding with said pivot from said ball-and-socket joint housing through said joint opening;
    an electrode electrically insulated against said ball-and-socket joint housing and arranged in a wall of said bearing shell at a spaced location from said joint ball, said electrode and said joint ball being electrically insulated against each other via said bearing shell; and
    a duct provided in said ball-and-socket joint housing, an electrically insulated electric line being connected to said electrode and being electrically insulated against said ball-and-socket joint housing, said electrically insulated line extending through said duct and from said ball-and-socket joint housing.

10. The ball-and-socket joint according to claim 9, wherein said electrically insulated electric line is directly electrically connected to said electrode.

11. The ball-and-socket joint according to claim 9, wherein said electrode has a rectangular cross section.

12. The ball-and-socket joint according to claim 9, wherein said bearing shell has a cylindrical section and at least one of an inclined and a frustum-shaped section, said electrode arranged in said inclined section of said bearing shell.

13. The ball-and-socket joint according to claim 9, wherein said electrode has a ring-shaped design.

14. The ball-and-socket joint in accordance with claim 9, wherein said bearing shell has a tapered or frustum-shaped section.

15. The ball-and-socket joint in accordance with claim 14, wherein said a tapered or frustum-shaped section adjoining a tapered or frustum-shaped section of said ball-and-socket joint housing, said electrode being arranged in the tapered or frustum-shaped section of said bearing shell.

16. The ball-and-socket joint in accordance with claim 15, wherein said joint ball has a diameter greater than transverse diameter of said duct.

17. A ball-and socket joint comprising:
- a ball-and-socket joint housing with a joint opening, said ball-and-socket joint housing being composed of an electrically conductive material;
- a bearing shell made of an insulating material arranged in said housing;
- a ball pivot made of an electrically conductive material, the ball pivot having a joint ball and a pivot mounted rotatably and pivotably with said joint ball in said bearing shell and protruding with said pivot from said ball-and-socket joint housing through said joint opening;
- an electrode arranged in a wall of said bearing shell at a spaced location from said joint ball, said electrode and said joint ball being electrically insulated with respect to each other via said bearing shell disposed between said electrode and said joint ball, said electrode being electrically insulated with respect to said ball-and-socket joint housing, said electrode being designed as a printed circuit board; and
- an electrode signal connection line connected to said electrode and extending from said electrode through said ball-and-socket joint housing, said electrode signal connection line being electrically insulated with respect to said ball-and-socket joint housing.

* * * * *